US00PP36577P2

(12) United States Plant Patent
Fleck et al.

(10) Patent No.: US PP36,577 P2
(45) Date of Patent: Apr. 1, 2025

(54) ***PRUNUS* HYBRID ROOTSTOCK NAMED 'PIHy17EYNem'**

(50) Latin Name: ***Prunus* hybrid**
Varietal Denomination: PIHy17EYNem

(71) Applicant: Sierra Gold Nurseries, Inc., Yuba City, CA (US)

(72) Inventors: Charles Edward Fleck, Yuba City, CA (US); Reid Robinson, Yuba City, CA (US)

(73) Assignee: Sierra Gold Nurseries, Inc., Yuba City, CA (US)

( * ) Notice: Subject to any disclaimer, the term of this patent is extended or adjusted under 35 U.S.C. 154(b) by 0 days.

(21) Appl. No.: 18/796,216

(22) Filed: Aug. 6, 2024

(51) Int. Cl.
*A01H 5/06* (2018.01)
*A01H 6/74* (2018.01)

(52) U.S. Cl.
USPC ..... Plt./180

(58) Field of Classification Search
USPC ..... Plt./156, 180
See application file for complete search history.

*Primary Examiner* — Susan McCormick Ewoldt
(74) *Attorney, Agent, or Firm* — Michelle Bos Legal LLC

(57) ABSTRACT

A new and distinct *Prunus* hybrid tree named 'PIHy17EYNem' useful as a rootstock and notable for increased vigor imparted to scions, excellent root strength, tolerance of wet soils and reduced susceptibility to root-and crown-rots caused by *Phytophthora* species.

6 Drawing Sheets

Latin name: *Prunus* hybrid.
Variety denomination: 'PIHy17EYNem'.

BACKGROUND OF THE VARIETY:

'PIHy17EYNem' is a new and distinct *Prunus* hybrid tree developed for use as a rootstock. 'PIHy17EYNem' was selected from among seedlings obtained from the controlled cross of female parent *Prunus cerasifera* 'Early Yellow' (not patented) and male parent *Prunus persica* x *Prunus davidiana* 'Nemaguard' (not patented) carried out at Yuba City, California in 2019. The 'PIHy17EYNem' plum tree was selected for further observation and was first propagated by hardwood cuttings at Yuba City, California in 2021. The variety has since been asexually reproduced through successive generations and has been observed to remain true to type.

BRIEF DESCRIPTION OF THE VARIETY

'PIHy17EYNem' was selected because of the high vegetative vigor it imparts to grafted scions. 'PIHy17EYNem' vigor is significantly higher than both parents, about 125% to 130% of the vigor of *Prunus* rootstock 'AP 1' (U.S. Plant Pat. No. 16,272, sold as Krymsk® 86) and 135% of the vigor of plum almond rootstock 'PAC 941' (U.S. Plant Pat. No. 21,556). The root strength (tree anchorage evaluated subjectively as resistance to being pushed over) of 'PIHy17EYNem' is excellent, higher than both parents and similar to 'AP 1'. 'PIHy17EYNem' is further distinguished from 'PAC 941' by its influence on scion ripening; 'Nonpareil' almond scions grafted on 'PIHy17EYNem' ripen 5 days later than on 'PAC 941'. 'PIHy17EYNem' is tolerant of wet soils.

BRIEF DESCRIPTION OF THE PHOTOGRAPHS

The photographs were taken in 2023 at Yuba City, California. The tree shown is 2 years old.

Figure 1:
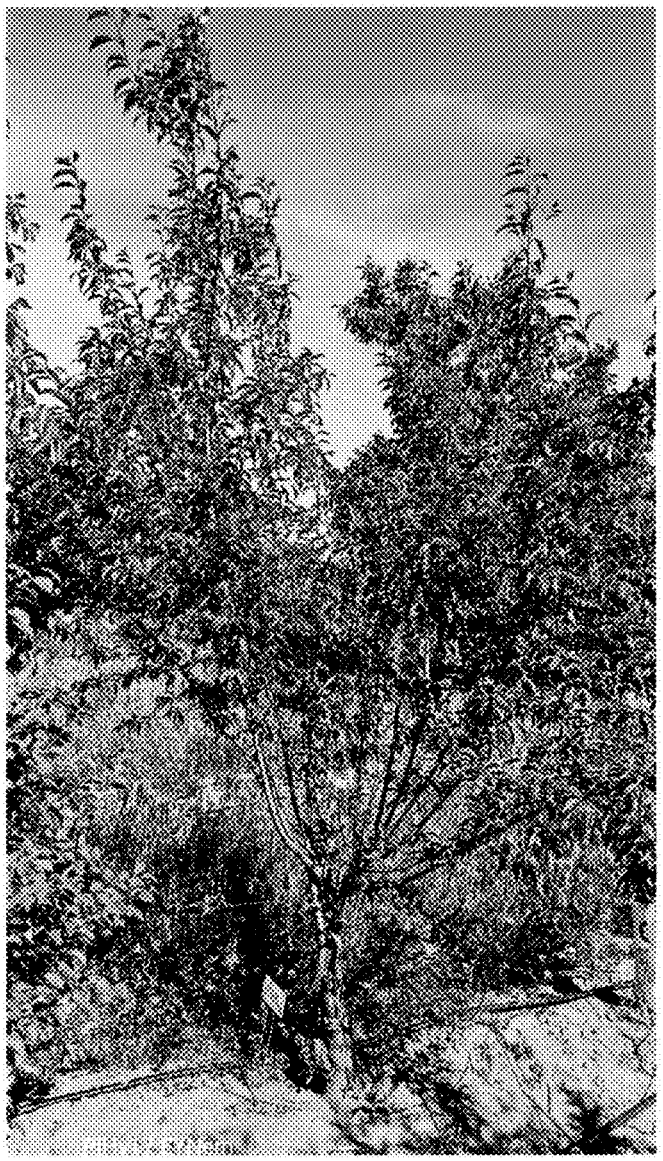
Figure 2:
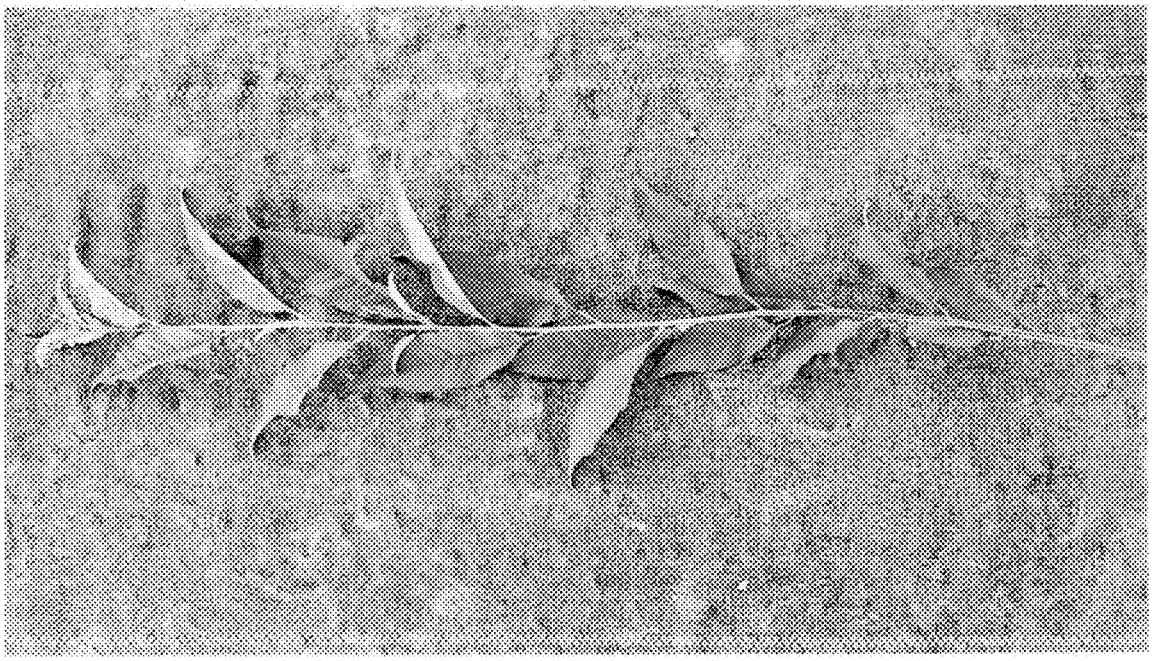
Figure 3:
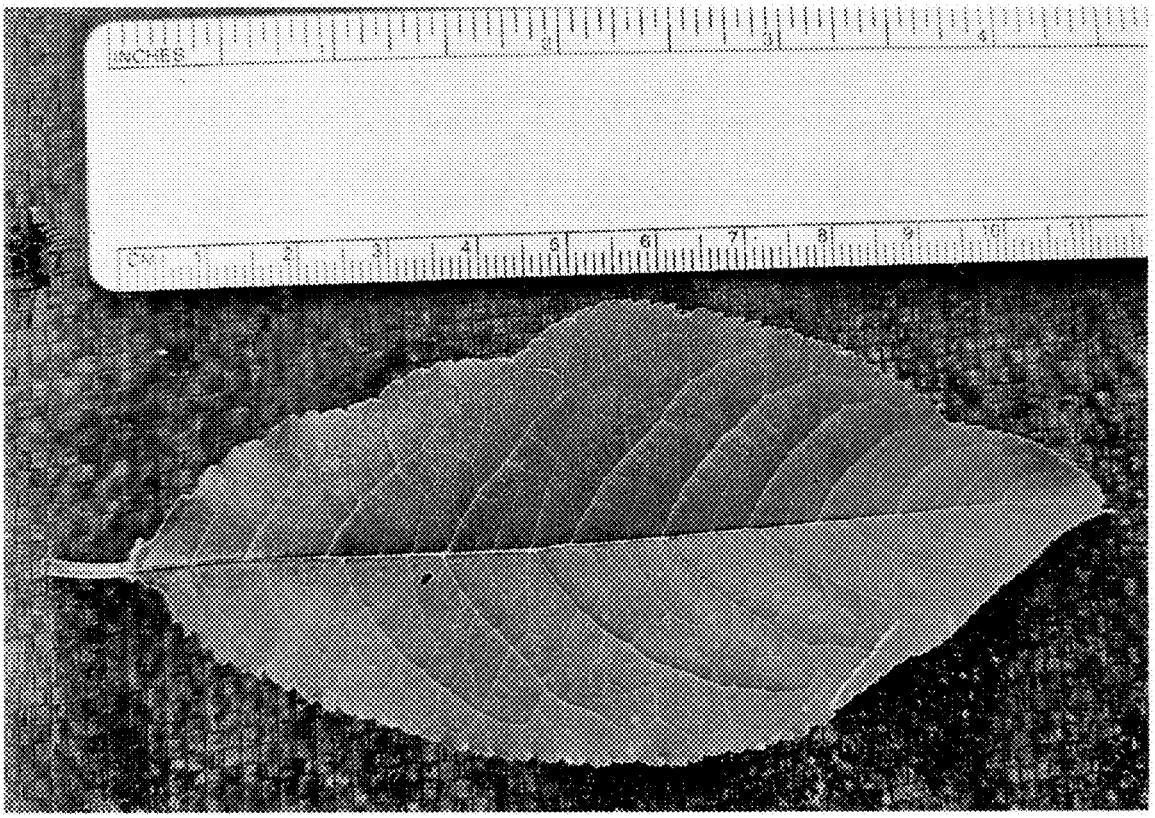
Figure 4:
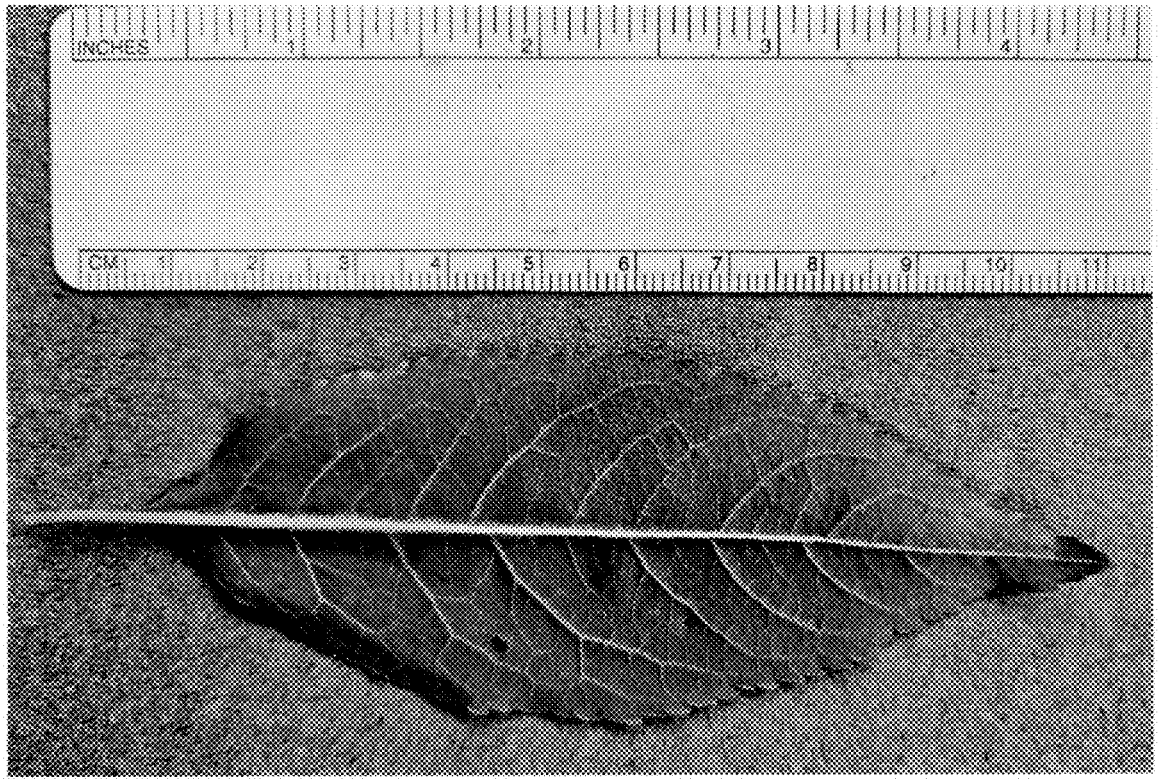
Figure 5:
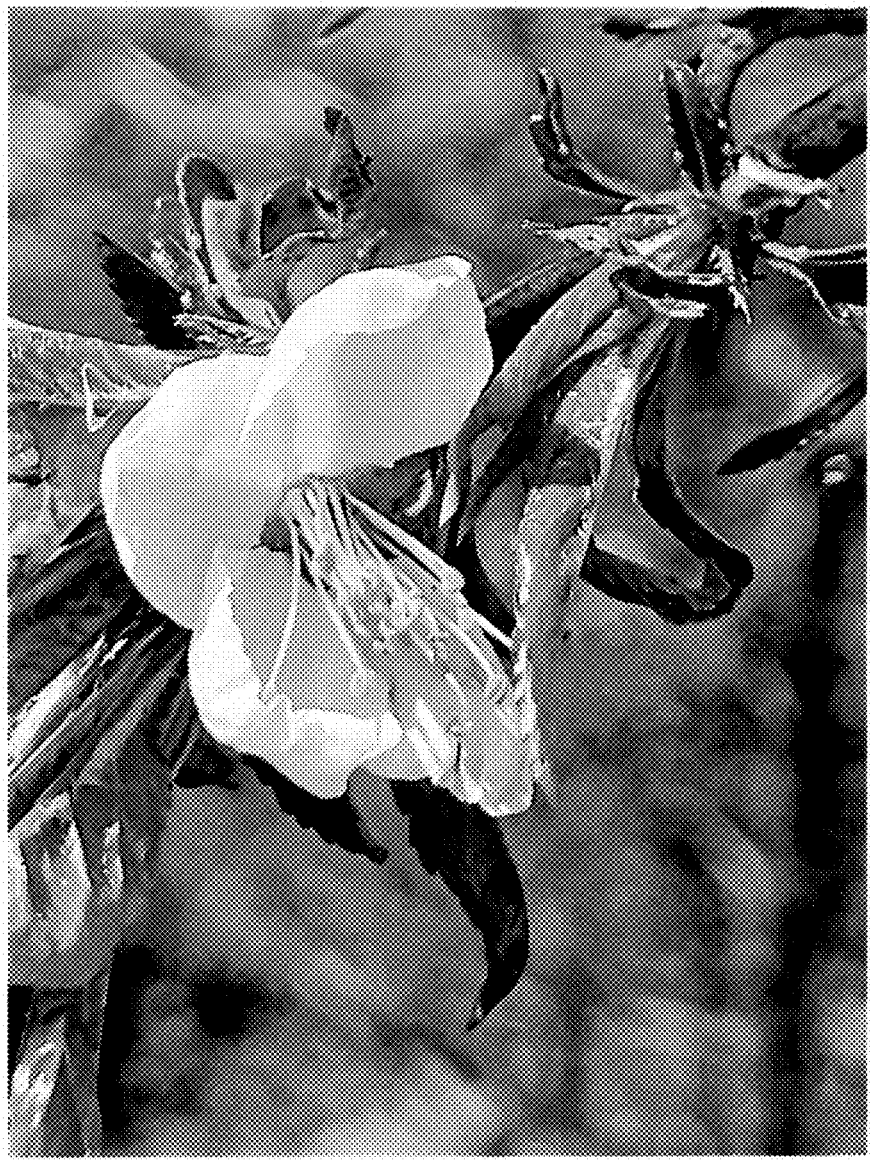
Figure 6:
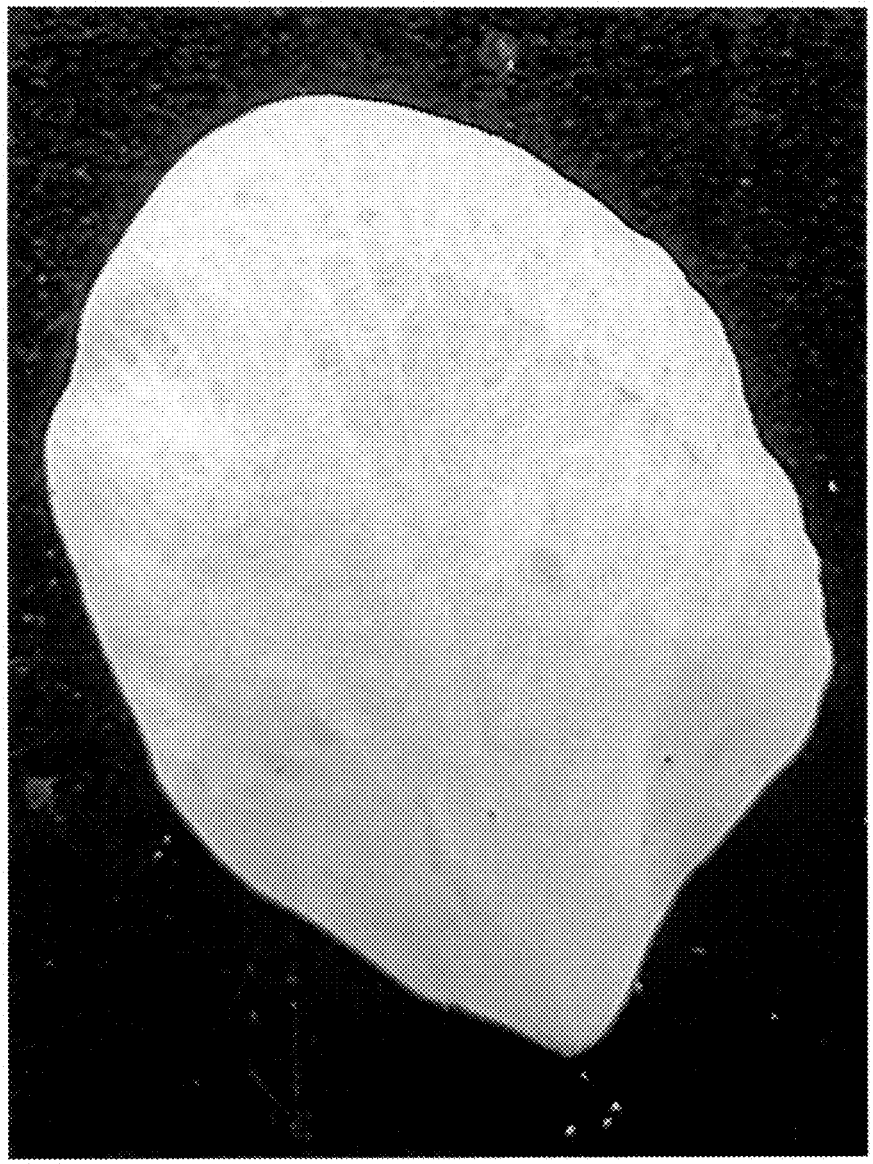

FIG. 1 shows a tree of the claimed variety;
FIG. 2 shows a branch and leaves of the claimed variety;
FIG. 3 shows the upper surface of a leaf of the claimed variety;
FIG. 4 shows the lower surface of a leaf of the claimed variety;
FIG. 5 shows a flower of the claimed variety; and,
FIG. 6 shows a flower petal of the claimed variety.

DETAILED BOTANICAL DESCRIPTION OF THE VARIETY

The following detailed botanical description is based on observations made at Yuba City, California during the 2023 growing season of 2-year-old trees grown on their own roots. All colors are described according to The R.H.S. Colour Chart (Royal Horticultural Society, London, 6$^{th}$ edition). The characteristics described will vary somewhat depending upon cultural practices and climatic conditions and will vary with location and season. Quantified measurements are expressed as an average of measurements taken from a number of individual plants of the new variety. The measurements of any individual plant or any group of plants of the new variety may vary from the stated average.

Tree:

*Vigor.*—High; 125% to 130% higher than 'AP 1'.
*Habit, shape.*—Upright, open-centered vase.
*Height.*—3.3 m.
*Spread.*—2.7 m.
*Trunk diameter at* 30 *cm above the ground.*—8.9 cm (four trunks).
*Bark texture.*—Slightly rough due to raised lenticels.
*Bark color.*—Greyed-orange 174A and 177A.
*Lenticel size.*—0.6 cm to 1 cm.
*Lenticel color.*—Grey-brown 199D.
*Lenticel density per cm*$^2$.—0 to 4.
*Root sprouts* (*suckering*).—None or very few.

*Root system*.—Highly branched, stiff woody root system with strong resistance to pushing and shearing forces; tolerant to wetter soils having a higher-than-average clay constituent content.

Branch (fruiting branches located at around 1 m above the ground):
*Length*.—30 cm to 65 cm.
*Diameter*.—2.7 to 4.0 cm.
*Crotch angle*.—45° to 60°.
*Bark color*.—Greyed-orange 165A.
*Bark texture*.—Very smooth.
*Lenticel length*.—<1 mm.
*Lenticel width*.—<1 mm.
*Lenticel color*.—Greyed-orange 163A.
*Lenticel density per cm²*.—0 to 6.

One year old shoot:
*Length*.—193 cm to 210 cm.
*Diameter*.—0.6 cm to 1.8 cm.
*Pubescence*.—Absent.
*Color*.—Greyed-orange 165A.
*Internode length*.—1.0 cm to 1.5 cm.
*Lenticel length*.—<1 mm.
*Lenticel width*.—<1 mm.
*Lenticel color*.—Greyed-orange 163A.
*Lenticel density per cm²*.—0 to 6.

Flower buds:
*Stage described*.—Dormant.
*Quantity per spur*.—Two.
*Bud shape*.—Conical.
*Apex shape*.—Acute.
*Length*.—5 mm to 6 mm.
*Diameter*.—2 mm to 3 mm.
*Color*.—Brown 200C.

Flowers:
*Diameter of fully open flower*.—16 mm to 18 mm.
*Depth of fully open flower*.—1.4 mm to 1.6 mm.
*Relative position of petal margin*.—Free.
*Pedicel length*.—1.0 mm to 1.2 mm.
*Pedicel diameter*.—1.2 mm to 1.4 mm.
*Pedicel color*.—Yellow-green 143B.
*Number of flowers per cluster*.—1 to 2.
*Date of first bloom*.—2 Apr. 2023.
*Date of full bloom*.—6 Ap. 2023.
*Pollination requirement*.—Sexually sterile rootstock requires no pollination.

Petals:
*Number per flower*.—5.
*Length*.—14.5 mm to 15.6 mm.
*Width*.—11.4 mm to 13.7 mm.
*Petal shape*.—Obovate.
*Apex shape*.—Rounded.
*Base shape*.—Attenuate.
*Margin*.—Entire.
*Color of upper surface*.—White NN155D.
*Color of lower surface*.—White NN155B.

Pistil: Absent.

Stamens:
*Quantity*.—28.
*Anther length*.—1.0 mm to 1.1 mm.
*Anther color*.—Yellow 20A.
*Filament diameter*.—0.2 mm.
*Filament color*.—White NN155D.
*Pollen*.—Present, abundant.
*Pollen color*.—Greyed-orange 163A.

Sepals:
*Quantity*.—5.
*Color*.—Yellow-green 145A with red-purple 60C.
*Sepal shape*.—Deltoid.
*Apex shape*.—Sub-obtuse.
*Length*.—3.3 mm to 4.5 mm Length.
*Margin*.—Serrate.

Leaves:
*Length*.—6.9 cm to 11.2 cm.
*Width*.—2.7 cm to 5.2 cm.
*Blade margin*.—Serrate.
*Leaf shape*.—Attenuate, elliptic.
*Apex shape*.—Acute.
*Base shape*.—Cuneate.
*Attitude in relation to shoot*.—Outward.
*Color of upper surface*.—Yellow-green 146A.
*Color of lower surface*.—Yellow-green 146C Petiole:
*Length*.—6.8 mm to 8.3 mm.
*Diameter*.—0.6 mm to 0.9 mm.
*Color*.—Green 141D.
*Glands*.—Present; circular, diameter <1 mm; color yellow 1A.

Fruit: Plant is sterile and forms no fruit.

Chilling requirement: Approximately 600 chill units, similar to Myrobalan-plum hybrid rootstocks 'AP 1' and 'PAC 941' (U.S. Plant Pat. No. 21,556, sold as Rootpac®R).

Disease resistance/susceptibility: The rootstock has extremely good tolerance to heavy, wet soils and is less susceptible to root-and crown-rots caused by *Phytophthora* species.

Market use: Vigorous rootstock for almond (*Prunus dulcis*), prune plum (*Prunus domestica*), peach (*Prunus persica*) and apricot (*Prunus armeniaca*).

The invention claimed is:

1. A new and distinct *Prunus* hybrid tree named 'PIHy17EYNem' substantially as illustrated and described herein.

* * * * *